(12) United States Patent
Giamalva et al.

(10) Patent No.: US 9,238,073 B2
(45) Date of Patent: Jan. 19, 2016

(54) PHARMACEUTICAL COMPOSITION CONTAINING SYMPATHOMIMETIC AMINE SALT AND CO-DISTILLABLE ADDITIVE

(75) Inventors: David Hugh Giamalva, Glen Allen, VA (US); Gary Bruce Anderson, Bayswater (GB)

(73) Assignee: Wyeth LLC, New York, NY (US)

( * ) Notice: Subject to any disclaimer, the term of this patent is extended or adjusted under 35 U.S.C. 154(b) by 2325 days.

(21) Appl. No.: 11/402,504

(22) Filed: Apr. 12, 2006

(65) Prior Publication Data

US 2007/0243140 A1    Oct. 18, 2007

(51) Int. Cl.
| | |
|---|---|
| *A61K 47/18* | (2006.01) |
| *A61K 9/20* | (2006.01) |
| *A61K 31/137* | (2006.01) |
| *A61K 31/192* | (2006.01) |
| *A61K 31/205* | (2006.01) |
| *A61K 31/473* | (2006.01) |
| *A61K 31/485* | (2006.01) |
| *A61K 31/616* | (2006.01) |

(52) U.S. Cl.
CPC .............. *A61K 47/18* (2013.01); *A61K 9/2013* (2013.01); *A61K 31/137* (2013.01); *A61K 31/192* (2013.01); *A61K 31/205* (2013.01); *A61K 31/473* (2013.01); *A61K 31/485* (2013.01); *A61K 31/616* (2013.01)

(58) Field of Classification Search
CPC . A61K 31/137; A61K 31/192; A61K 31/205; A61K 31/473; A61K 31/485; A61K 31/616; A61K 47/18; A61K 9/2013
See application file for complete search history.

(56) References Cited

U.S. PATENT DOCUMENTS

| | | | |
|---|---|---|---|
| 3,832,460 | A | 8/1974 | Kosti |
| 5,681,577 | A | 10/1997 | Lech et al. |
| 6,136,864 | A | 10/2000 | Nichols et al. |
| 6,197,314 | B1 | 3/2001 | Einig |
| 6,359,011 | B1 | 3/2002 | Bess et al. |
| 6,495,529 | B1 | 12/2002 | Booth et al. |
| 6,852,891 | B2 | 2/2005 | Murray et al. |
| 2002/0082304 | A1 | 6/2002 | Bess et al. |
| 2003/0119915 | A1 | 6/2003 | Booth et al. |
| 2004/0166063 | A1 | 8/2004 | Siegel |
| 2005/0026298 | A1 | 2/2005 | Bickett et al. |

FOREIGN PATENT DOCUMENTS

| | | | |
|---|---|---|---|
| EP | EP 1 319 397 A | | 6/2003 |
| WO | WO 91/09591 A | | 7/1991 |
| WO | WO2004/0412328 A2 | | 5/2004 |
| WO | WO 2005/023236 A | | 3/2005 |
| WO | WO 2005/046727 A2 | * | 5/2005 |

* cited by examiner

*Primary Examiner* — Kara R McMillian
(74) *Attorney, Agent, or Firm* — Jeffrey M. Gold; Maureen P. O'Brien; Joseph F. Reidy

(57) ABSTRACT

A pharmaceutical composition is provided which contains a water soluble acid salt of a sympathomimetic amine, e.g., pseudoephedrine, and an additive, e.g., a volatile amine or other odorant, that is co-distillable, e.g., by steam distillation, with the sympathomimetic amine and/or its derivatives, e.g., its free base.

18 Claims, No Drawings

PHARMACEUTICAL COMPOSITION CONTAINING SYMPATHOMIMETIC AMINE SALT AND CO-DISTILLABLE ADDITIVE

TECHNICAL FIELD

The present invention relates generally to a pharmaceutical composition comprising sympathomimetic amine salt, wherein said amine is difficult to isolate for illicit drug manufacturing, especially by distillation.

BACKGROUND

Sympathomimetic compounds, as the name implies, exert biological effects similar to those produced by activation of the sympathetic nervous system. For example, the pharmaceutical compound pseudoephedrine acts as an indirect sympathomimetic agent by causing adrenergic nerve endings to release norepinephrine, thereby stimulating alpha- and beta-norepinephrine receptors, particularly in blood vessels of the upper respiratory tract. This, in turn, results in vasoconstriction and shrinkage of swollen tissues in the sinuses and nasal passages, rendering such compounds useful as decongestants.

Despite their legitimate uses, acid salts of sympathomimetic amines (SA), such as the ubiquitous pseudoephedrine hydrochloride, pseudoephedrine sulfate, ephedrine hydrochloride and phenylpropanolamine hydrochloride, are often utilized in the synthesis of illegal drugs such as methamphetamine, amphetamine, methcathinone, and cathinone. One of the most efficient starting materials in the synthesis of methamphetamine is ephedrine, which is heavily regulated and therefore difficult to obtain. Increasingly, pseudoephedrine, a diastereomer of ephedrine, is being used in the production of methamphetamine. Pseudoephedrine can be obtained from a pseudoephedrine salt, such as pseudoephedrine hydrochloride, which is a common ingredient in over-the-counter (OTC) medications.

Pseudoephedrine hydrochloride may be isolated from OTC medications by first suspending/dissolving the commercial products in water. The resulting slurry/solution is filtered and then treated with base to neutralize the amine salt, thereby producing pseudoephedrine free base. The free base, which has limited water solubility, is then extracted into a water immiscible solvent such as ether. This extraction serves as a purification step. Acidification to regenerate the amine hydrochloride followed by extraction into water is normally adequate to produce suitably pure pseudoephedrine hydrochloride. Alternatively, one may use the free base without regenerating the salt form.

It has thus been found desirable to formulate sympathomimetic amine-containing products in order to render isolation of the sympathomimetic amine more difficult or otherwise interfere with efforts to produce illegal drugs from common OTC medications, e.g., by altering reactants used to convert sympathomimetic amine to methamphetamine.

For example, U.S. Pat. No. 6,136,864 to Nichols et al. discloses incorporation of one or more denaturant compounds, to render commercially available medications containing sympathomimetic amine salts much less suitable as starting materials in the production of illegal drugs. The denaturant(s) exhibit chemical or physical properties which make the isolation of the pure sympathomimetic amine salt difficult or essentially infeasible, resulting in compromised yields of illicit product. The denaturant can be a compound, e.g., quinine, whose separation from sympathomimetic amine salts is difficult or essentially infeasible, so that the synthesis of illegal drugs from the compositions of the invention is rendered impracticable and/or produces illegal drugs in an adulterated form. Alternately, the denaturant is a material that physically interferes with the extraction of the sympathomimetic amine salts from the pharmaceutical products (i.e., emulsifies and/or alters viscosity of the pharmaceutical products in solution), so that the purification of the sympathomimetic amine salts from the pharmaceutical products is rendered impractical. In one aspect, the denaturant reacts to provide a product of "unpleasant taste, smell, emetic effect, etc.," e.g., sulfur-containing amino acids and nitrogen-containing denaturants.

U.S. Pat. No. 6,359,011 to Bess et al. and US 2002/0082304 to Bess et al. disclose a pharmaceutical composition comprising sympathomimetic amine salt and a combination inhibitor, e.g., amino polymer, which interferes with both the isolation of the amine as well as its conversion to another pharmacologically active compound, without altering amine release from the composition.

U.S. Pat. No. 6,197,314 to Einig discloses a pharmaceutical tablet whose active ingredient, e.g., pseudoephedrine, is blended with an extraction-preventing composition which contains i) surfactant, e.g., alkyl sulfonate and ii) a fat or gel former, e.g., hydroxypropylmethylcellulose. The tablet produces a creamy emulsion when extraction of the active is attempted.

US2004/0166063 to Siegel discloses a method for marking a pharmaceutical product, container or pharmaceutical packaging system with a scent to establish identity or source of a product.

U.S. Pat. No. 6,495,529 and US2003/0119915 to Booth, et al. disclose pharmaceutical compositions which include (−)-pseudoephedrine, substantially free of (+)-pseudoephedrine, and a carrier. (−)-Pseudoephedrine, like (+)-pseudoephedrine, acts as an effective decongestant, but without the latter's side effects and drug interactions. Moreover, (−)-pseudoephedrine's reduction yields (R)-methamphetamine, which has only one-tenth the psychoactivity of (S)-methamphetamine derived from (+)-pseudoephedrine, which discourages illicit drug manufacture from these pharmaceutical compositions.

US2005/0026298 to Bickett et al. provides a method for modifying liquid anhydrous ammonia to discourage theft by adding a dye, e.g., a xanthene dye, say, rhodamine, which stains any object in subsequent contact with the liquid anhydrous ammonia. The dye can be visible to the naked eye and so discourages the use of such liquid ammonia in illicit drug manufacture, inasmuch as the dye can stain illicit products, production areas and equipment, the manufacturers themselves and, ultimately, the drug user.

U.S. Pat. No. 6,852,891 to Murray et al. discloses a way to inhibit or prevent the use of anhydrous ammonia in a dissolving metal reduction process such as that used to convert pseudoephedrine, etc., to methamphetamine. The method adds to the anhydrous ammonia a chemical reagent capable of scavenging solvated electrons generated when metal is dissolved in the ammonia. Murray et al. use stoichiometric compounds capable of undergoing a finite number of one-electron reduction processes, e.g., urea, alpha-tocopherol (vitamin E) and derivatives thereof, pentamethylchromanol, trichloroethylene and 1,1,1,2-tetrafluoroethane. Alternately, catalytic compounds accelerating reaction of electrons with the amonia solvent to produce amide anion and hydrogen gase can be used, e.g., Fe(III) citrate, ferrocene, 2-chloro-6-(trichloromethyl)pyridine and 1,1,1,2-tetrafluoroethane. Murray et al. at col. 5, lines 63 to 67 teach that "[c]hoosing a compound which possesses a boiling point close to that of ammonia increases the likelihood that the compound will be carried over during a distillation of the ammonia, thus making removal of the compound from ammonia very difficult." Use of this anhydrous ammonia substantially reduces methamphetamine yield.

All of the above references are incorporated herein by reference in their entirety.

Despite the various methods set out above which inhibit the isolation of sympathomimetic amines or otherwise inhibit illicit synthesis efforts, techniques have been developed which limit the effectiveness of these methods. For example, certain distillation techniques can be employed to separate denaturants from sympathomimetic amines.

Accordingly, it would be advantageous to provide additional methods for preventing or deterring illegal conversion of sympathomimetic amine compounds while maintaining OTC availability, particularly for overcoming distillation-based isolation of sympathomimetic amines.

SUMMARY

In one aspect, the present invention relates to a pharmaceutical composition comprising a mixture which contains: i) a water soluble acid salt of a sympathomimetic amine, and ii) an additive that is co-distillable with the sympathomimetic amine and/or its derivatives.

In some embodiments of this aspect, the additive inhibits reduction of the sympathomimetic amine and/or its derivatives.

In other embodiments of this aspect of the invention, the additive is co-distillable with the free base of the sympathomimetic amine, e.g., as obtained from aqueous alkali treatment of a salt of the sympathomimetic amine.

In still other embodiments of this aspect of the invention, the additive is co-steam distillable with the sympathomimetic amine and/or its derivatives, e.g., the free base of the sympathomimetic amine.

In yet other embodiments of this aspect of the invention, the additive is co-steam distillable with the free base of the sympathomimetic amine or its derivatives and is, furthermore, substantially unextractable from the sympathomimetic amine and/or its derivatives. The additive can be substantially unextractable by one or more various methods, e.g., methanol extraction, n-hexane extraction, and/or acid/base extraction. For present purposes, the term "substantially unextractable" means that less than about 10-20% of the total additive is removed by a single extraction step.

In yet still other embodiments of this aspect of the invention, the additive, e.g., volatile amine, exhibits a vapor pressure at 100° C. of at least about 2 mmHg, preferably at least about 3 mmHg, say, from about 5 to about 100 mmHg.

In other embodiments of this aspect of the invention, the additive exhibits a vapor pressure at 100° C. ranging from about 0.1 to about 10 times, say, about 0.2 to about 2.0 times that of the sympathomimetic amine.

In still other embodiments of this aspect of the invention, the additive is present in an amount ranging from about 0.01 to about 5 moles, say, from about 0.5 to about 2 moles per mole of the sympathomimetic amine salt.

In yet other embodiments of this aspect of the invention, the sympathomimetic amine is selected from the group consisting of ephedrine, phenylpropanolamine, and pseudoephedrine, e.g., pseudoephedrine.

In still yet other embodiments of this aspect of the invention, the additive comprises a volatile amine having a vapor pressure at about 95-100° C. of at least about 2 mmHg, say, at least about 5 mmHg. Typically, said volatile amine has the formula $R^1R^2R^3N$ wherein $R^1$, $R^2$ and $R^3$ are each individually selected from —H, phenyl, aryl, substituted aryl, alkyl-substituted phenyl, aryl-substituted phenyl, benzyl-substituted phenyl, and/or $C_1$ to $C_8$ alkyl. Exemplary amines include but are not limited to phenethylamine, tributylamine, dibutylamine, octylamine, N-benzylethylamine, and ortho, meta, and para aminoacetophenone (acetylaniline).

In yet still other embodiments of this aspect of the invention, the additive comprises an odorant. Typically, the odorant is co-distillable with the sympathomimetic amine or its derivatives, say, by steam distillation, e.g., where the sympathomimetic amine is present as a free base.

In other embodiments of this aspect of the invention, the additive comprises an odorant. Exemplary odorants include but are not limited to camphor, ethyl citrate, menthol, methyl anthranil, methyl anthranilate, isoamyl acetate, geranyl acetate, linalool, alpha ionone, ortho-nitroacetophenone, alpha terpineol, and ortho-aminoacetophenone. The additive can comprise a mixture of two or more odorants selected from the group consisting of esters, alcohols, hydrocarbons and amines. Exemplary of such mixtures are commercially available fruit flavorants, e.g., grape flavorant.

In still other embodiments of this aspect of the invention, the odorant is present in an amount sufficient to provide a product derived from distillation overhead wherein the product contains the odorant in an amount which is detectable by the mammalian sense of smell.

In yet other embodiments of this aspect of the invention, the odorant is present in an amount sufficient to provide a product derived from distillation overhead wherein the product contains the odorant in an amount of at least about 10 ppm by weight, say, from about 50 ppm to about 200 ppm, by weight.

In yet still other embodiments of this aspect of the invention, the pharmaceutical composition has a total odorant content of no greater than about 0.1 moles, per mole of sympathomimetic amine and/or its derivatives. Typically said total odorant content ranges from about 0.0001 to about 0.1 moles, per mole of sympathomimetic amine salt, say, from about 0.0005 to about 0.05 moles, per mole of sympathomimetic amine salt.

In still yet other embodiments of this aspect of the invention, the pharmaceutical composition comprises at least one further active ingredient selected from the group consisting of a fever reducer/pain reliever, an antihistamine, a cough suppressant/antitussive, an antihistamine/topical analgesic, and an expectorant. Typically, the fever reducer/pain reliever is selected from the group consisting of acetaminophen, acetylsalicylic acid, indomethacin, acemethacin, sulindac, piroxicam, ibuprofen, naproxen, e.g., naproxen sodium, and ketoprofen, the antihistamine is selected from the group consisting of loratadine, pyrilamine, triprolidine HCl, doxylamine succinate, diphenhydramine HCl, diphenhydramine citrate, brompheniramine maleate, and chlorpheniramine maleate, the cough suppressant/antitussive is selected from the group consisting of dextromethorphan, chlophedianol, diphenhydramine HCl and diphenyhydramine citrate, the antihistamine/topical analgesic is diphenhydramine HCl, and the expectorant is selected from the group consisting of guaifenesin, N-acetyl cysteine, and carbomethoxy cysteine. The sympathomimetic amine can be selected from the group consisting of ephedrine, phenylpropanolamine, and pseudoephedrine, e.g., pseudoephedrine in an amount ranging from about 10 mg to about 200 mg, say, about 30 mg. Other pharmaceutically acceptable salt forms of these active ingredients may also be used.

In another aspect, the present invention relates to a method of reducing the isolatability of a water soluble acid salt of a sympathomimetic amine from a pharmaceutical composition containing the acid salt of a sympathomimetic amine, which comprises including within the pharmaceutical composition a compound which is co-distillable with the sympathomimetic amine and/or its derivatives, e.g., free base, in an amount sufficient to reduce the purity of the amine or its derivatives recovered from a distillation overhead, as compared to the purity otherwise effected but in the absence of the included compound.

In certain embodiments of this aspect of the invention, the compound is co-steam distillable with the sympathomimetic amine and/or its derivatives.

In other embodiments of this aspect of the invention, the compound is substantially incapable of separation from the sympathomimetic amine and/or its derivatives by a method or methods selected from the group consisting of solvent extraction, precipitation, simple distillation, and crystallization In still other embodiments of this aspect of the invention, the compound is co-distillable with the free base of the sympathomimetic amine.

In yet another aspect, the present invention relates to a method for relieving symptoms of rhinitis in a mammal, which method comprises administering a decongestive effective amount of a pharmaceutical composition comprising: a water soluble acid salt of a sympathomimetic amine in admixture with an additive that is co-distillable with the sympathomimetic amine and/or its derivatives.

In certain embodiments of this aspect of the invention, the additive can be co-steam distillable.

In other embodiments of this aspect of the invention, the additive comprises an odorant.

In still another aspect, the present invention relates to a pharmaceutical composition comprising a mixture of: i) a water soluble acid salt of a sympathomimetic amine, and ii) an additive that is co-distillable with the sympathomimetic amine and/or its derivatives, which mixture is in combination with at least one of the group consisting of pharmaceutically acceptable diluents, excipients, carriers, stabilizers, binders, buffers, lubricants, coating agents, preservatives, emulsifiers and suspension agents. Typically, the composition is in the form of a capsule, tablet, liquid, suspension, or powder, say, a tablet.

DETAILED DESCRIPTION

Sympathomimetic Amines

Sympathomimetic amines are those compounds which cause vasoconstriction in the vascular bed of the nasal mucosa which results in a shrinking of the engorged mucous membranes and thus promote drainage and improve nasal air flow. As used herein, the term "sympathomimetic amine" refers to a pharmaceutically acceptable acid addition salt of a compound which may have asymmetric centers and occur as racemates, racemic mixtures, individual diastereomers, or enantiomers, with all isomeric forms being included in the present invention. Such salts are soluble in water, typically to an extent of at least about 30 g/100 g of water, as measured at any temperature ranging from about 10° to about 100° C., say, e.g., at about 25° C. For present purposes, derivatives of the salt include free base, HCl and sulfate, with the HCl salt being especially preferred.

In a particularly preferred embodiment of the present invention, the sympathomimetic amines are used commercially as nasal decongestants. Specific examples of acid salts of sympathomimetic amine decongestants commonly found in OTC medications include: phenylephrine hydrochloride, phenylpropanolamine hydrochloride, pseudoephedrine hydrochloride, pseudoephedrine sulfate and ephedrine hydrochloride.

Examples of illegal drugs which are synthesized from sympathomimetic amines include, but are not limited to, methamphetamine, amphetamine, methcathinone, and cathinone. The preparation of illegal drugs from sympathomimetic amines is known to those of skill in the art and occurs through a variety of oxidative or reductive reactions.

Co-Distillable Additives

Additive(s) suited to use in the present invention relate to a compound or mixture of compounds which exhibit properties sufficiently similar to those of the sympathomimetic amine, such that the additives are difficult or impossible to separate out of mixtures with the sympathomimetic amine or its derivatives, especially its free base, by techniques that include conventional distillation processes, e.g., steam distillation. Thus, the additive should exhibit low water solubility, typically less than about 5 g/100 g of water, say, from about 0.1 to about 2 g/100 g of water at a temperature of 100° C. Additionally, the additive should also exhibit some volatility from a solution of water and alkali, with partial pressures of at least about 2 mmHg, say, between about 5 mmHg and about 50 mmHg at 100° C. Thus, if the additive were present in a tablet containing pseudoephedrine, it would volatilize along with the pseudoephedrine, so that the condensate from steam distillation would contain a mixture of the two compounds rather than pure pseudoephedrine alone in water. Amounts as low as 1 mg of additive in a tablet containing a typical dose of, say, about 30 mg of sympathomimetic amine, e.g., pseudoephedrine, can at least partially encumber the isolation of the sympathomimetic amine, although higher amounts, typically from about 10 to about 500 parts, say, from about 33 to about 200 parts, total additive per 100 parts of sympathomimetic amine, by weight, would be more effective.

The additives used in the present invention must be essentially non-toxic at the levels used in pharmacological preparations, e.g., in tablets. Thus, additive should be approved for use in a pharmaceutical product. Ideally, the additive is a compendial material listed in the United States Pharmacopeia-National Formulary (USP-NF) or the approved "generally recognized as safe" (GRAS) list. Additives that meet these requirements include menthol and camphor (USP/NF), and triacetin, ethyl citrate (or triethyl citrate), and methyl anthranilate (GRAS).

In addition to its "safe" or "non-toxic" character, the co-distillable additive used in the present invention can, in certain embodiments, advantageously interfere with other methods of purification, besides distillation. Such other methods include recrystallization, solvent extraction, simple distillation, and precipitation. Additives such as menthol or camphor would not be readily separable from sympathomimetic amine, e.g., pseudoephedrine, by either a methanol extraction, or by a simple acid/base extraction, although an acid/base extraction with a preliminary filtration of the tablet mixture in water would largely remove these additives. In contrast, a volatile amine additive would be especially suited to use in the present invention inasmuch as it would co-steam distill with sympathomimetic amine and would not separate therefrom upon acid/base extraction.

These additives can be further characterized by an ability to reduce the overall potency of the illegal drugs which are synthesized from sympathomimetic amines, with which the additives are mixed. The reduction in potency of the mixture can be effected by mere dilution alone, or by, say, interference with the reduction to methamphetamine by competing with pseudoephedrine for the reducing agent. Alternately, the additive can impart a characteristic to the mixture, for example, a characterizing or even objectionable odor, a characterizing or even objectionable flavor, a color, etc. which reduces marketability of an illegal drug prepared from sympathomimetic amine/additive mixture, or which readily "tags" the drug as contraband.

Odorants

In certain embodiments of the invention, the co-distillable additive(s) of the present invention can be odorants, i.e., compounds which exhibit a characteristic odor, and in some cases, a characteristic flavor as well, particularly during purification and/or conversion of sympathomimetic amines in illegal drug synthesis, or in the product of the illegal synthesis itself. Odorants are especially useful inasmuch as they can be effective when added in relatively small amounts as compared to additives which are used solely as diluents or additives that interfere with subsequent chemical reactions for converting sympathomimetic amine compounds to illegal drugs. Pharmaceutical formulations of the present invention which contain odorants should contain them in an amount sufficient to impart a strong odor to any derived fraction that contains sympathomimetic amine, especially where such fractions are derived from distillation. Suitable levels of odorant additives which can deter conversion of sympathomimetic amine-containing formulations to illegal drugs can range from about 0.01 to about 10 parts, say, from about 0.1 to about 1 part, total additive per 100 parts of sympathomimetic amine, by weight.

The odor effected by the odorant can be unpleasant, or merely pungent enough to be detected by the mammalian sense of smell, especially that of a human. The odor may be released during the preparation of illegal drugs, and thereby render such preparation distasteful and/or serve as a recognizable signal to law enforcement that illegal drugs are being prepared at a particular location. Illegal drugs prepared from starting materials that comprise the odorant may themselves retain a distasteful odor and/or taste.

Exemplary odorants include synthetic flavor oils and flavoring aromatics and/or natural oils, extracts from plants, leaves, flowers, fruits and so forth and combinations thereof, which are co-distillable with the sympathomimetic amine or its derivatives, e.g., its free base. These odorants can include cinnamon oil, oil of wintergreen, peppermint oils, clove oil, bay oil, anise oil, eucalyptus, thyme oil, cedar leave oil, oil of nutmeg, oil of sage, oil of bitter almonds, vanilla, citrus oil, and cassia oil. Especially useful are mixtures of slightly volatile (i.e., with boiling points from 150° C. to 250° C. at atmospheric pressure) flavorant compounds such as can be found in commercially available natural and/or synthetic fruit flavorings. Flavorants which have been found to be particularly useful as odorants in the present invention, include lemon, orange, grape, lime and grapefruit, and fruit essences, including apple, pear, peach, strawberry, raspberry, cherry, plum, pineapple, apricot and mixtures thereof, with grape flavorants being especially preferred. These fruit flavorings are typically complex mixtures of flavor components, each at a very low level. Inasmuch as these mixtures typically contain mixtures of compounds taken from several different chemical classes, e.g., esters, alcohols, hydrocarbons, and, in some cases, amines, no single separation step is likely to effectively remove all such classes of compounds. The amount of odorant/flavorant added to the pharmaceutical composition may depend on a number of factors, including the desired organoleptic effect. Flavors can be present in any amount as desired by the artisan of ordinary skill in the art. Particularly preferred flavors are the grape and cherry flavors and citrus flavors such as orange.

For present purposes, a suitable odorant can be selected from the group consisting of methyl anthranil, methyl anthranilate, isoamyl acetate, linalool, alpha ionone, ortho-nitroacetophenone, ortho-aminoacetophenone, and geranyl acetate, which can be found in natural and synthetic flavors, and which have strong, distinctive odors. In one aspect of the invention, a single compound with a distinct and characteristic odor is used as odorant. Thus, where alpha ionone is added as odorant, informed law enforcement personnel would recognize alpha ionone's violet scent as a bellwether of illicit drug conversion activity.

The odorant compounds can be readily steam distilled, so they will co-steam distill with pseudoephedrine or ephedrine. In addition, many of these can be extracted with sympathomimetic amine, e.g., pseudoephedrine, by solvent extraction with polar or non-polar organic solvents, as well as by acid/base extraction techniques as known by those skilled in the art.

Additionally, when present at sufficiently high levels, typically, from about 33 to about 300 parts additive, say, from about 50 to about 100 parts additive, per 100 parts of sympathomimetic amine, specific odorants can inhibit one or more of the reactions, e.g., reduction, used to convert the sympathomimetic amine to an illegal drug. At levels below this, an odorant can deter misuse of commercially available sympathomimetic amines by imparting a very strong odor to a material, even after multiple attempts to isolate the sympathomimetic amine. Thus, an illicit drug manufacturer (or ultimate user) would likely conclude that the resulting "isolate" contains one or more additional components and is less than pure, and so would reject such material or subject it to additional purification steps at additional cost and inconvenience. Moreover, where a specific odorant, e.g., a standard flavorant, is used, it imparts a specific odor to an area in which conversion to illicit drugs occurs, which can serve to tip off law enforcement agencies to illegal activity where a certain odor becomes associated with illicit drug production. The slightly volatile odorants tend to condense and are thus absorbable by walls, carpeting, clothing, etc. provide added complications to illicit drug manufacture.

Volatile Amines

In certain non-limiting embodiments of the invention, the odorant may contain nitrogen, e.g., as a volatile amine. Examples of such co-distillable nitrogen-containing odorants include mono, di and trialkylamine hydrochlorides, mono- and di-alkyl benzylamines, mono- and di-alkyl aryl amines, succinamide and glutaric acid diamide. When such nitrogen-containing compounds are subjected to illegal reaction conditions, odoriferous ammonia, low molecular weight amines and low molecular weight diamines such as putrescine and cadaverine can be produced. The foregoing nitrogen-containing denaturants can develop their unpleasant odor during the alkaline extraction and isolation steps of a conversion process used to derive an illegal drug from a legal sympathomimetic amine.

To summarize, an additive of the present invention should exhibit co-distillability with the sympathomimetic amine with which it is combined. Preferably, it is steam distillable from aqueous alkali, inasmuch as the latter is typically present upon conversion of the sympathomimetic amine to its free base. The additive must further be safe in the amounts in which it is present in the pharmaceutical composition. Such safety can be evidenced by approval of the additive as an excipient in a 'Monograph' pharmaceutical product in the USA, or its presence on the GRAS list or in the USP-NF. Optionally, the additive provides, in addition to co-distillability, one or more additional obstacles to the separation or purification of sympathomimetic amine from commercially available products. Such would include solubility in methanol, ether, hexane, or other organic solvents, as well as partitionability into an organic solvent phase from an aqueous base phase.

Pharmaceutical Compositions

The term "pharmaceutical composition" as used herein and in the accompanying claims is to be understood as defining compositions of which the individual components or ingredients are themselves pharmaceutically acceptable, e.g. where oral administration is foreseen, suitable or acceptable for oral application.

The amount of additive(s) and sympathomimetic amine salts in any composition of the present invention can be in a ratio from about 100:1 to about 1:1000, preferably from about 10:1 to about 1:10. More preferably, the amount of additive(s) and sympathomimetic amine salts in any composition of the present invention can be in a ratio from about 3:1 to about 1:3. Most preferably, the amount of additive(s) and sympathomimetic amine salts in any composition of the present invention is in a ratio from about 2:1 to about 1:2.

Generally the total quantity of additive(s) in a unit dose preparation may be varied or adjusted from about 0.1 mg to about 750 mg according to the particular application and the potency of the sympathomimetic amine salt. When pseudoephedrine hydrochloride is the sympathomimetic amine salt, the concentration of the additive(s) is typically in a range from about 0.3 mg to about 300 mg; most preferably, in a range from about 10 mg to about 90 mg; and most preferably, in a range from about 15 mg to about 60 mg, say, about 30 mg. When phenylpropanolamine hydrochloride is the sympathomimetic amine salt, the concentration of the additive(s) is typically in the range from about 7.5 mg to about 750 mg; more preferably, in the range from about 25 mg to about 225 mg; most preferably, in the range from about 37.5 mg to about 75 mg.

The present invention is also directed to methods of preparing the additive/sympathomimetic amine salt combinations. The combinations are prepared by adding an effective amount of at least one additive to a sympathomimetic amine salt-containing pharmaceutical composition. The additive(s) may be added individually or as a mixture to the pharmaceutical composition. The present invention is also directed to products made by such methods of preparation.

Pharmaceutical compositions comprising the additive(s) and the sympathomimetic amine salt(s) (and when desired other pharmaceutical actives in an intimate admixture with a pharmaceutical carrier) may be prepared according to conventional pharmaceutical compounding techniques. The compositions may take a wide variety of forms depending on the form of preparation desired for administration, e.g., intravenous, oral or parenteral. The compositions according to this invention may, for example, take the form of tablets, capsules, granules, powders, or lozenges, or liquid preparations such as solutions and non-aqueous suspensions, with tablets being especially preferred.

The compositions may be formulated using conventional carriers or excipients according to well-established techniques. Without being limited thereto, such conventional carriers or excipients include diluents, binders and adhesives (e.g., cellulose derivatives and acrylic derivatives), lubricants (e.g., magnesium or calcium stearate, or vegetable oils, polyethylene glycols, talc, sodium lauryl sulphate, polyoxyl ethylene monostearate), disintegrants, colorants, flavorings, preservatives, sweeteners and miscellaneous materials, such as buffers and adsorbents as needed, in order to prepare a particular composition.

Non-aqueous suspensions may be obtained by dispersing the additive/sympathomimetic amine compositions in a suitable non-aqueous based vehicle, optionally with the addition of suitable viscosity enhancing agent(s) (e.g., hydrogenated edible fats, aluminum stearate, etc.). Suitable non-aqueous vehicles include, for example, almond oil, arachis oil, soybean oil or fractionated vegetable oils such as fractionated coconut oil. Preservative(s) (e.g., methyl, ethyl, propyl or butyl-hydroxybenzoates, sodium benzoate or sorbic acid, etc.) may be included as appropriate.

A wide variety of medicaments may further be present in the denaturant/sympathomimetic amine combinations of the present invention. The medicaments may be selected from a wide variety of drugs and their acid addition salts. Suitable categories of drugs that may be employed may vary widely. Illustrative categories and specific examples include a) antitussives, such as dextromethorphan, dextromethorphan hydrobromide, noscapine, carbetapentane citrate, and chlorphedianol hydrochloride; b) antihistamines, such as chlorpheniramine maleate, phenindamine tartrate, pyrilamine maleate, doxylamine succinate, phenyltoloxamine citrate, diphenhydramine hydrochloride, promethazine and triprolidine; c) antiasthmatic drugs, J2-adrenergics, e.g. salbutamol (albuterol), terbutaline, carbuterol, broxaterol, aminophylline, and theophylline; d) analgesics such as acetaminophen; and e) non-steroidal antiinflammatory drugs (NSAID), such as acetylsalicylic acid, indomethacin, acemethacin, sulindac, piroxicam, ibuprofen, naproxen, ketoprofen; expectorants, such as guaifenesin, N-acetyl cysteine, and carbomethoxy cysteine. Other pharmaceutically acceptable salt forms of these active ingredients may also be used.

The following examples illustrate methods for preparing the sympathomimetic amine salt with co-distillable additive compositions of the invention. Any combinations, compositions or products described herein are used for known indications treated by sympathomimetic amines.

EXAMPLES

Example 1 (Comparative)

Conventional sympathomimetic amine-containing pharmaceutical tablets (Advil Allergy Sinus) are prepared according to well known formulation procedures. The tablets each contain 200 mg ibuprofen as pain reliever/fever reducer, 30 mg pseudoephedrine hydrochloride as decongestant and 2 mg chlorpheniramine maleate as antihistamine. The tablets further contain as inactive ingredients carnauba wax, croscarmellose sodium, FD&C red no. 40 aluminum lake, FD&C yellow no. 6 aluminum lake, glyceryl behenate, hypromellose, iron oxide black, microcrystalline cellulose, polydextrose, polyethylene glycol, pregelatinized starch, propylene glycol, silicon dioxide, starch, and titanium dioxide.

Example 2

Sympathomimetic amine-containing pharmaceutical tablets are prepared according to well known formulation procedures, in accordance with Example 1, but further comprising the addition of methyl anthranilate additive which is co-distillable with the pseudoephedrine free base, in an amount sufficient to provide about 6 mg of additive per tablet. The additive is added in such a way as to be well-mixed with the pseudoephedrine hydrochloride.

Example 3

Sympathomimetic amine-containing pharmaceutical tablets are prepared according to well known formulation procedures, in accordance with Example 1, but further comprising the addition of menthol additive which is co-distillable with the pseudoephedrine free base, in an amount sufficient to provide about 10 mg of additive per tablet.

Example 4

Sympathomimetic amine-containing pharmaceutical tablets are prepared according to well known formulation procedures, in accordance with Example 1, but further comprising the addition of a commercially available grape flavorant, available from Ungerer & Company, of Bethlehem, Pa. USA, or WILD Flavors, Inc., Erlanger, Ky. USA, comprising a mixture of esters, alcohols and hydrocarbons, which additive is co-distillable with the pseudoephedrine free base, in an amount sufficient to provide about 5 mg of additive per tablet.

Example 5

Sympathomimetic amine-containing pharmaceutical tablets are prepared according to well known formulation procedures, in accordance with Example 1, but further comprising the addition of alpha ionone, which additive is co-distillable with the pseudoephedrine free base, in an amount sufficient to provide about 5 mg of additive per tablet.

Example 6

The tablets prepared in Examples 1 to 6 are subjected to processes intended to isolate the sympathomimetic amine component using steam distillation as described, e.g., in "Modern Experimental Organic Chemistry," Third Edition, by Royston R. Roberts et al., pages 44 to 49). This method is consistent with methods known to be used in the isolation of pseudoephedrine for illicit purposes. The alkaline aqueous mixture comprising a slightly volatile component of low water solubility is heated to boiling. The vapors are condensed and collected to provide a condensate containing both water and the slightly volatile component, which is extracted with an immiscible organic solvent, such as toluene, to provide a solution of pseudoephedrine in the organic solvent. The pseudoephedrine is further isolated by evaporating off the solvent. Alternately, the aqueous condensate is acidified to convert the pseudoephedrine back to the non-volatile HCl salt, which is either collected as a precipitate or isolated by evaporating the mixture to dryness. Each recovered pseudoephedrine containing portion is then analyzed by HPLC or GC to quantitate the amount of pseudoephedrine obtained and assess its purity.

Pseudoephedrine is extractable from the tablets of Example 1 which lacks the co-distillable additive and yields pseudoephedrine of approximately 95% purity without further purification.

The recovered pseudoephedrine salt-containing portions from Examples 2 to 5 exhibit less than about 90% purity. In addition, each such portion exhibits a strong and distinctive odor.

While preferred embodiments have been shown and described, various modifications and substitutions may be made without departing from the spirit and scope of the invention. Accordingly, it is to be understood that the present invention has been described by way of example and not by limitation.

The invention claimed is:

1. A pharmaceutical composition comprising a mixture which contains: i) a water soluble acid salt of a sympathomimetic amine, and ii) an additive that is co-distillable with the sympathomimetic amine, wherein less than 10-20 weight percent of the additive is separated from the mixture by a single extraction.

2. The pharmaceutical composition of claim 1 wherein said additive inhibits reduction of said sympathomimetic amine.

3. The pharmaceutical composition of claim 1 wherein said additive is co-distillable with the free base of said sympathomimetic amine.

4. The pharmaceutical composition of claim 1 wherein said additive is co-steam distillable with said sympathomimetic amine.

5. The pharmaceutical composition of claim 4 wherein said additive is co-steam distillable with the free base of said sympathomimetic amine.

6. The pharmaceutical composition of claim 4 wherein said additive is co-steam distillable with the free base of said sympathomimetic amine and is substantially unextractable from said sympathomimetic amine.

7. The pharmaceutical composition of claim 6 wherein said additive is substantially unextractable by methanol extraction, n-hexane extraction, and/or acid/base extraction.

8. The pharmaceutical composition of claim 1 wherein the additive exhibits a vapor pressure at 100° C. which ranges from 0.1 to about 10 times that of the sympathomimetic amine.

9. The pharmaceutical composition of claim 1 wherein the additive is present in an amount ranging from about 0.01 to about 2 moles, per mole of sympathomimetic amine salt.

10. The pharmaceutical composition of claim 1 wherein the additive is present in an amount ranging from about 0.1 to about 0.5 moles, per mole of sympathomimetic amine salt.

11. The pharmaceutical composition of claim 1 wherein the sympathomimetic amine is selected from the group consisting of ephedrine, phenylpropanolamine, and pseudoephedrine.

12. The pharmaceutical composition of claim 1 wherein the sympathomimetic amine is pseudoephedrine.

13. The pharmaceutical composition of claim 1 wherein said additive is a volatile amine having a vapor pressure at 100° C. of at least about 2 mmHg.

14. The pharmaceutical composition of claim 13 wherein said volatile amine has the formula $R^1R^2R^3N$ wherein $R^1$, $R^2$ and $R^3$ are each individually selected from —H, phenyl, alkyl-substituted phenyl, aryl-substituted phenyl, benzyl-substituted phenyl and/or $C_1$ to $C_8$ alkyl.

15. The pharmaceutical composition of claim 1 that comprises a further active ingredient selected from the group consisting of a fever reducer/pain reliever, an antihistamine, a cough suppressant/antitussive, an antihistamine/topical analgesic, and an expectorant.

16. The pharmaceutical composition of claim 15 wherein said fever reducer/pain reliever is selected from the group consisting of acetaminophen acetylsalicylic acid, indomethacin, acemethacin, sulindac, piroxicam, ibuprofen, naproxen, and ketoprofen, said antihistamine is selected from the group consisting of loratadine, pyrilamine, triprolidine HCl, doxylamine succinate, diphenhydramine HCl, diphenhydramine citrate, brompheniramine maleate, and chlorpheniramine maleate, said cough suppressant/antitussive is selected from the group consisting of dextromethorphan, chlophedianol, diphenhydramine HCl and diphenhydramine citrate, and said expectorant is selected from the group consisting of guaifenesin. N-acetyl cysteine, and carbomethoxy cysteine.

17. The pharmaceutical composition of claim 16 wherein said sympathomimetic amine is pseudoephedrine in an amount ranging from about 10 mg to about 200 mg.

18. The pharmaceutical composition of claim 16 wherein said sympathomimetic amine is pseudoephedrine in an amount of about 30 mg.

* * * * *